(12) United States Patent
Shimada et al.

(10) Patent No.: US 9,439,414 B2
(45) Date of Patent: Sep. 13, 2016

(54) SPERM DILUENT SOLUTION AND METHOD FOR ARTIFICIAL INSEMINATION USING SAME

(75) Inventors: Masayuki Shimada, Higashi-Hiroshima (JP); Tetsuji Okazaki, Bungoono (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 780 days.

(21) Appl. No.: 13/378,560

(22) PCT Filed: Jun. 17, 2010

(86) PCT No.: PCT/JP2010/060320
§ 371 (c)(1),
(2), (4) Date: Apr. 20, 2012

(87) PCT Pub. No.: WO2010/147194
PCT Pub. Date: Dec. 23, 2010

(65) Prior Publication Data
US 2012/0197068 A1     Aug. 2, 2012

(30) Foreign Application Priority Data
Jun. 17, 2009  (JP) .................................. 2009-144703

(51) Int. Cl.
*A01N 1/02* (2006.01)
*C12N 5/076* (2010.01)
*A61K 35/12* (2015.01)

(52) U.S. Cl.
CPC ............. *A01N 1/0221* (2013.01); *C12N 5/061* (2013.01); *A61K 35/12* (2013.01); *C12N 2500/14* (2013.01); *C12N 2517/10* (2013.01)

(58) Field of Classification Search
CPC ........ A01N 1/0221; A01N 1/00; A01N 1/02; A01N 1/021; C12N 5/061; A61D 19/02; A61D 19/021; A61D 19/022; A61D 19/024; A61D 19/025; A61D 19/027; A61K 35/12; A61K 35/52; A61B 17/42; A61B 17/425; A61B 17/435

USPC .............. 600/33–35; 435/404, 405, 406, 408
See application file for complete search history.

(56) References Cited

U.S. PATENT DOCUMENTS 6,071,231 A * 6/2000 Mendoza et al. ................ 600/35
6,130,086 A * 10/2000 Nakazawa et al. ........... 435/325

(Continued)

FOREIGN PATENT DOCUMENTS

| CN | 1712519 | 12/2005 |
|---|---|---|
| EP | 1147774 | 10/2001 |

(Continued)

OTHER PUBLICATIONS

Ochsenkuehn et al, The Relationship Between Immunisuppresive Activity and Immunoregulatory Cytokines in Seminal Plasma: Influence of Sperm Autoimmunity and Seminal Leukocytes, Journal of Reproductive Immunology, 2006.

(Continued)

*Primary Examiner* — Charles A Marmor, II
*Assistant Examiner* — Carrie R Dorna
(74) *Attorney, Agent, or Firm* — Perkins Coie LLP; Viola T. Kung

(57) ABSTRACT

A sperm diluent of the present invention contains a chelating agent such as EDTA and/or, EGTA, which forms a complex with a calcium ion, in a base diluent. Further, the sperm diluent contains an immunosuppressive factor such as a steroid hormone and/or, a cytokine, which suppresses migration of leukocytes. By diluting frozen sperm with this sperm diluent followed by performing artificial insemination, death of the sperm before fertilization and phagocytosis of the sperm and embryos by leukocytes in the uterus can be suppressed, allowing enhancement of the conception rate and the implantation rate.

4 Claims, 10 Drawing Sheets

(56) References Cited

U.S. PATENT DOCUMENTS

| | | | |
|---|---|---|---|
| 6,890,708 B2* | 5/2005 | Matthijs-Rijsenbilt et al. | 435/2 |
| 2003/0215782 A1* | 11/2003 | Kusakabe et al. | 435/2 |
| 2004/0265831 A1* | 12/2004 | Arav et al. | 435/6 |
| 2010/0003748 A1* | 1/2010 | Baker | 435/325 |

FOREIGN PATENT DOCUMENTS

| | | | |
|---|---|---|---|
| JP | 2000-119101 | | 4/2000 |
| JP | 2008-063235 | | 3/2008 |
| WO | WO03065979 | * | 8/2003 |

OTHER PUBLICATIONS

Okazaki, Tetsuji et al, "Development of New Pig Sperm Freeze-thaw Handling Method Focusing on Seminal Plasma, and Application to Artificial Insemination", Livestock Technology, Nov. 2008, p. 21-24 (2008).

Okazaki, Tetsuji et al, "Development of Artificial Insemination Method by the Pig Frozen Sperm Using a Sperm Protecting Agent and an Implantation Promoter", Livestock Technology, Dec. 2009, p. 8-11 (2009).

Manual for Using Pig Frozen Semen (Tazaemon NIWA ed., 1989), Artificial Inseminator's Association of Japan.

Ashworth, PJ et al., "Survival of ram spermatozoa at high dilution: protective effect of simple constituents of culture media as compared with seminal plasma", CSIRO Publishing—Reproduction, Fertility and Development, vol. 6, No. 2, Jan. 1, 1994, p. 173.

Frydrychova, et al., "Relation of seminal plasma components and prlr gene incidence to morphologically abnormal spermatozoa of boars", Research in Pig Breeding, vol. 1, No. 2, Jan. 1, 2007, pp. 22-25.

Luconi, et al., "Extracellular Calcium Negatively Modulates Tyrosine Phosphorylation and Tyrosine Kinase Activity during Capacitation of Human Spermatozoa", Biology of Reproduction, vol. 55, Jan. 1, 1996, pp. 207-216.

Robertson, S. A. et al., "Seminal fluid signaling in the female reproductive tract: Lessons from rodents and pigs", Journal of Animal Science, vol. 85, No. 3, Mar. 1, 2007, pp. E36-E44.

Rozeboom, et al., "The effect of spermatozoa and seminal plasma on leukocyte migration into the uterus of gilts", Journal of Animal Science, vol. 77, Jan. 1, 1999, pp. 2201-2206.

Szczygiel, Monika A. et al., "Expression of Foreign DNA is Associated with Paternal Chromosome Degradation in Intracytoplasmic Sperm Injection-Mediated Transgenesis in the Mouse", Biology of Reproduction, vol. 68, May 1, 2003, pp. 1903-1910.

Young, L. G. et al., "Calcium Ions and Control of the Motility of Sea Urchin Spermatozoa", J. Reprod. Fert., vol. 41, Dec. 1, 1974, pp. 371-378.

Jin, Y et al., "Effects of Supplementation of EDTA Extender Containing Trehalose on the Freezability of Boar Spermatozoa", Chinese Journal of Veterinary Science. vol. 27 (1)., Jan. 31, 2007, 5 Pages.

Baoying, Lin et al., "The effects of levamisole on surface bound antisperm antibodies on different position of motile spermatozoa", Chinese Journal of Reproductive Health; 16(3), Mar. 2005, pp. 146-149.

Zubing, Cao et al., "Progress on Freeze-drying and cryopreservation technology of mammalian sperm", Anima Husbandry & Veterinary Medicine; 41(2), Feb. 2009, pp. 96-99.

Fujii, S. et al., "Immunomodulatory Properties of Seminal Plasma in Reproduction: Review of Literature", Journal of the Aomori Society of Obstetricians and Gynecologists, vol. 21, No. 1, English translation of relevant portions included (2 pages), 2006, pp. 16-31.

Kahiwazaki, Naomi et al., "Researches on characteristics of freeze-dried sperm and offspring production from the sperm in the pig", Journal of Azabu University, vol. 11,12, 2005, pp. 114-122.

* cited by examiner

SPERM DILUENT SOLUTION AND METHOD FOR ARTIFICIAL INSEMINATION USING SAME

CROSS-REFERENCE TO RELATED APPLICATIONS

This application claims priority to International Patent Application No. PCT/JP2010/060320 filed 17 Jun. 2010, and claims priority to Japanese Patent Application No. 2009-144703 filed 17 Jun. 2009, both of which are incorporated herein by references in their entirety.

TECHNICAL FIELD

The present invention relates to a sperm diluent to be used for dilution of frozen sperm for artificial insemination of a non-human mammal, especially pig or the like, and a method of artificial insemination using the sperm diluent.

BACKGROUND ART

Artificial insemination is an important technology in the field of animal husbandry. Artificial insemination of livestock has so far been carried out mainly with cows. However, the conception rate still needs to be improved, and, in terms of livestock other than cows, the artificial insemination technology has not yet been established.

For example, since natural crossing is mainly carried out in the Japanese swine industry, boars must be kept and a high cost is therefore required. Further, since the body weight of a boar becomes not less than 300 kg, the operation is accompanied by a risk. Further, since much labor is required for natural crossing, efficient development of good breeds (e.g., improvement to obtain races excellent in the meat quality and the litter size) by crossing has been prevented.

At present, in some cases in the Japanese swine industry, artificial insemination is carried out. However, since, in the current system, liquid semen is sent only after ordering by pig farmers, the time lag may results in missing of estrus in cases where the estrus suddenly occurred.

Therefore, development of a technology which allows storage of frozen semen in each pig farmer and thereby enables to deal with sudden occurrence of estrus of a sow has been demanded. However, in the cases of artificial insemination using frozen semen in pigs, the mobility of the sperm is remarkably poor after freeze-thawing; the fertilization ability of the sperm is low; the conception rate varies depending on factors such as the season and the race; the conception rate is low; and the litter size is small (Non-patent Literature 1 and Non-patent Literature 2); so that artificial insemination using frozen semen is not carried out almost at all in the field of the swine industry.

PRIOR ART DOCUMENTS

Non-Patent Literatures

Non-patent Literature 1: Tetsuji Okazaki and 2 other authors, "Influences of Osmotic Pressure and Glycerol Concentration of Diluent on Motility and Implantation Rate of Pig Freeze-thawed Sperm", 107th Meeting of Japanese Society of Animal Science, General Lecture, V29-29.

Non-patent Literature 2: Manual for Using Pig Frozen Semen (Tazaemon Niwa ed., 1989), Artificial Inseminator's Association of Japan.

DISCLOSURE OF INVENTION

Problem to be Solved by the Invention

The present inventors proposed an artificial insemination method using frozen sperm prepared by collecting sperm followed by removal of seminal plasma and freezing (Japanese Patent Application No. 2007-325313). By artificial insemination of frozen sperm thawed in a diluent containing seminal plasma, enhancement of the conception rate has been achieved.

However, there is a problem in that, since seminal plasma contains pathogens such as bacteria, seminal plasma cannot be used for producing "SPF (Specific Pathogen Free) pigs", which have drawn attention in view of safety of food.

Further, since the characters of the seminal plasma to be added to the diluent vary among individuals and depending on the season, the conception rate and the implantation rate are likely to be unstable.

Further, boars must be kept to secure the seminal plasma.

The present invention was made in view of the above-described facts, and aims to provide a sperm diluent with which, even without inclusion of seminal plasma therein, a conception rate equivalent to or higher than the rate obtained with a seminal plasma-containing diluent can be obtained, and an artificial insemination method using the sperm diluent.

Means for Solving the Problems

The sperm diluent, which is the first mode of the present invention, comprises a chelating agent which forms a complex with a calcium ion.

Further, the chelating agent comprises preferably EGTA.

Further, the chelating agent comprises preferably EGTA and EDTA.

Further, the sperm diluent preferably comprises an immunosuppressive factor which suppresses migration of leukocytes.

Further, the immunosuppressive factor comprises one or more selected from steroid hormone and cytokine.

The steroid hormone comprises preferably one or more selected from cortisol and cortisol derivative.

Further, the cortisol derivative comprises preferably one or more selected from dexamethasone, prednisone and hydrocortisone.

Further, the cytokine comprises preferably one or more selected from macrophage migration inhibitory factor and Serpin E1.

Further, the sperm diluent is preferably used for diluting frozen sperm prepared by removal of seminal plasma and freezing.

Further, the frozen sperm is preferably frozen sperm of a non-human mammal.

Further, the non-human mammal is preferably a multiparous animal.

Further, the multiparous animal is preferably a pig.

In the artificial insemination method, which is the second mode of the present invention, frozen sperm prepared by removal of seminal plasma from semen collected from a non-human mammal and freezing is diluted with the sperm diluent, to prepare artificial semen; and the artificial semen is injected into the uterus of the non-human mammal, to carry out artificial insemination.

Further, a multiparous animal is preferably used as the non-human mammal.

Further, a pig is preferably used as the multiparous animal.

Effect of the Invention

Since the sperm diluent of the present invention does not contain seminal plasma at all, there is no problem of bacterial infection, and can therefore be used for production of specific-pathogen-free SPF pigs.

Further, since seminal plasma is not used, there is no influence of the seasons and differences among individuals from which the seminal plasma is collected, so that stable artificial insemination can be realized.

Further, since seminal plasma is unnecessary, there is no need to keep many boars for securing seminal plasma, which is advantageous.

Figure 1:
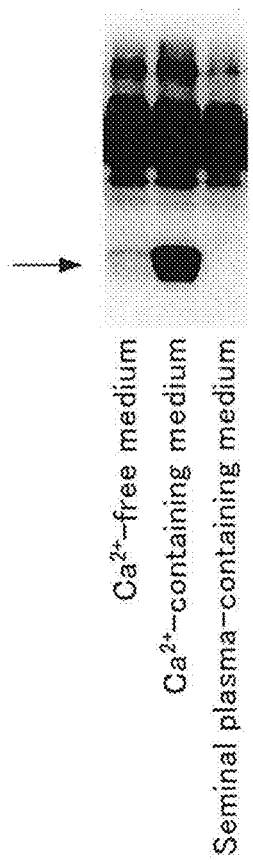
FIG. 1 is a diagram showing results of detection of phosphorylation of tyrosine residues in the sperm proteins in Experimental Example 1.

BEST MODE FOR CARRYING OUT THE INVENTION (Sperm Diluent)

The present inventors discovered that, in frozen sperm, the sperm die due to occurrence of a functional damage after thawing, leading to decrease in the fertility in artificial insemination, and that this functional damage is not observed in cases where a diluent supplemented with seminal plasma is used, leading to a high reproductive performance. The present inventors further discovered that, in this functional damage, the increase of calcium ions level influences the motility of sperm and phosphorylation of tyrosine residues of proteins, thereby completing the sperm diluent of the present mode.

In the sperm diluent of the present technique, a chelating agent, which forms a complex with a calcium ion, is contained in the later-mentioned base diluent. The inclusion of the chelating agent in the sperm diluent suppresses phosphorylation of the sperm proteins caused by involvement of calcium ions upon thawing of frozen sperm, resulting in decrease of the functional damage.

More particularly, in the middle piece of sperm, mitochondria rich region, where the energy (ATP) to be used for movement of the sperm is generated. When calcium ions act on mitochondria (more particularly, activate enzymes for producing ATP in mitochondria), production of ATP is accelerated, leading to rapid movement of the sperm, while too early activation of sperm causes death of the sperm before the sperm reach the oviduct.

In a sperm diluent of the present mode, a chelating agent is contained in the diluent, and the chelating agent forms a complex with a calcium ion, thereby preventing calcium ions from acting on sperm mitochondria.

The sperm diluent of the present mode is obtained by adding a chelating agent which forms a complex with a calcium ion to a base diluent.

Here, the base diluent means a diluent prepared such that collected semen can be stored therein at room temperature for a certain period without deterioration of the function of the sperm in the semen, which diluent is a liquid containing components such as glucose, sodium citrate, sodium bicarbonate, EDTA-2Na, citric acid, Tris and/or potassium chloride. The base diluent is not restricted as long as the base diluent is a liquid usually used in this field, and examples of the base diluent include Modena solution (0.15 M glucose, 26.7 mM sodium citrate, 11.9 mM sodium hydrogen carbonate, 15.1 mM citric acid, 6.3 mM EDTA-2Na, 46.6 mM Tris and 1,000 IU/ml penicillin).

The chelating agent is not restricted as long as the chelating agent is a substance which forms a complex specifically with a calcium ion, and ethylene glycol tetraacetic acid (EGTA (ethylene glycol Bis(2-aminoethyl)-N,N,N',N'-tetraacetic acid)) is preferably used. Since EGTA forms a complex specifically with a calcium ion, the action of calcium ions on sperm mitochondria can be effectively suppressed.

Further, together with EGTA, ethylenediaminetetraacetic acid (EDTA) is preferably used. EDTA is a substance which forms complexes with, in addition to a calcium ion, various divalent ions such as a magnesium ion and zinc ion.

By adding both EDTA and EGTA, calcium ions which have not been chelated with EDTA can be chelated with EGTA, and most of the calcium ions existing in the base diluent can be finally chelated. For example, in cases where only EDTA is used as a chelating agent, the concentration of EDTA in the base diluent needs to be high in order to chelate all the calcium ions with EDTA. Since the base diluent contains various divalent ions other than calcium ions, such as magnesium ions and zinc ions, excessive chelation of these divalent ions may also occur in cases where the EDTA concentration is too high, affecting the sperm function (fertilization). Therefore, both EDTA and EGTA are preferably added.

Based on the later-mentioned experimental results, in cases where both EDTA and EGTA are added, the EDTA and EGTA concentrations in the sperm diluent are preferably about 3 to 9 mM and about 3 to 9 mM, respectively, more preferably 6.3 mM and 6 mM, respectively.

Further, in order to prevent sperm, embryos or the like from being englobed (bitted or attacked) by leukocytes in the uterus, the sperm diluent preferably contains an immunosuppressive factor. Since sperm are foreign substances for a female, invasion of sperm into the uterus causes migration of leukocytes such as neutrophils and macrophages, causing phagocytosis of the sperm, embryos or the like, which affects the implantation rate.

The implantation rate is the ratio of the number of fetuses in the uterus with respect to the number of eggs. Since, especially in a multiparous animal such as a pig, 10 to 20 eggs are released, it is necessary in view of the production efficiency to fertilize as much eggs as possible at once to allow a large number of fetuses to be born.

Since the above phagocytosis is not likely to occur in natural crossing, it is thought that seminal plasma in semen contains an immunosuppressive factor which suppresses migration of leukocytes and excessive increase in leukocytes, thereby preventing the subsequent attack to embryos.

Therefore, inclusion of an immunosuppressive factor, which can suppress migration of leukocytes, in the sperm diluent can suppress phagocytosis of sperm or embryos and realize improvement of the implantation rate.

As the immunosuppressive factor, steroid hormones and cytokines are preferred.

A preferred steroid hormone is cortisol, which is a component contained in seminal plasma. By inclusion of cortisol in the diluent, a function of cellular immunity is inhibited and migration of leukocytes and the like is thereby blocked. By this, phagocytosis of sperm or embryos is suppressed, and improvement of the implantation rate is realized.

In cases where the diluent is used for artificial insemination of pigs, the amount of cortisol to be added in the sperm diluent used for each time of artificial insemination is preferably about 100 ng to 10,000 ng. The amount of cortisol is more preferably 500 ng to 5,000 ng. This amount is almost the same as the amount of cortisol contained in the total seminal plasma emitted from a male pig during natural crossing.

Since cortisol is originally contained in seminal plasma, and decomposed and discharged to the outside of the body in 1 or 2 days after the injection into the uterus, and since cortisol is locally injected and does not spread throughout the body, the living body is not adversely affected, and there is no harmful influence such as production of deformed piglets.

Further, in terms of other steroid hormones, cortisol derivatives such as dexamethasone, prednisolone and hydrocortisone are also considered to chemically change into cortisol and thereby show a similar immunosuppressive action. Therefore, these steroid hormones may also be used.

Preferred examples of the cytokines include macrophage migration inhibitory factors (MIFs) and Serpin E1. Both the macrophage migration inhibitory factors and Serpin E1 are substances contained in seminal plasma.

Cytokines such as macrophage migration inhibitory factors and Serpin E1 are signal transducers and suppress unnecessary accumulation of leukocytes such as neutrophils and macrophages in the uterus, and hence have an immunosuppressive action.

(Method of Artificial Insemination)

Methods of artificial insemination using the above-mentioned sperm diluent will now be described. As an example, a method of artificial insemination of pigs will be described below.

Frozen sperm prepared by removal of seminal plasma from semen of a boar followed by freezing are thawed, and immediately after the thawing, the sperm are added to a sperm diluent to prepare an artificial semen. Alternatively, upon thawing of the frozen sperm, the frozen sperm may be added to the sperm diluent.

More particularly, the thawing of frozen sperm is carried out at 37° C. for 60 seconds in cases where frozen sperm prepared by filling sperm in a 5-ml straw followed by freezing the sperm are used; or carried out at 35° C. for 20 seconds, preferably at 37° C. for 20 seconds, more preferably at 70° C. for 8 seconds, most preferably at 60° C. for 8 seconds in warm water in the cases of a 0.5-ml straw. Alternatively, the sperm diluent may be directly added to the frozen sperm.

The volume of the artificial semen used for artificial insemination of a pig is about 50 ml each time, and the artificial semen may be prepared such that the final concentration of sperm is in the order of $1 \times 10^6$ cells/ml to $1 \times 10^9$ cells/ml, preferably in the order of $1 \times 10^8$ cells/ml.

Thereafter, by injecting the prepared artificial semen into the uterus of a sow in a state of estrus, artificial insemination can be carried out.

On about Day 114 after the artificial insemination, delivery occurs in the sow. After the delivery, piglets spend the suckling period for 20 to 40 days, followed by weaning, and about 4 days after the weaning, the sow comes into estrus again. Artificial insemination may be carried out in the same manner as described above at the time of the return of estrus in the sow. By carrying out artificial insemination in such a cycle, a larger number of piglets can be delivered during the life time of a sow.

The sperm diluent can be simply stored in a freezer. Therefore, the sperm diluent can be used after thawing when necessary, and can be easily used at the timing of estrus of a sow or the like.

As the frozen sperm to be diluted with the sperm diluent of the present mode, frozen sperm prepared by removal of seminal plasma from semen and freezing are preferably used. By this, artificial insemination can be carried out under complete sterile conditions, so that, for example, the sperm can be used also for production of specific-pathogen-free SPF pigs Further, depending on the species of the mammal, artificial insemination may be difficult since seminal plasma adversely affects freezing of sperm and hence cannot carry out the freezing. Even in such cases, by removing seminal plasma and freezing sperm, followed by diluting the frozen sperm with a sperm diluent of the present mode, artificial insemination can be carried out.

Further, the sperm diluent of the present mode may be used for artificial insemination of any non-human mammal.

Further, the sperm diluent of the present mode may be used for non-human mammals such as domestic animals, and may be suitably used for artificial insemination of multiparous animals. Since the implantation rate is high also in multiparous animals such as pigs, many fetuses can be delivered at one time, so that the production efficiency can be increased.

Further, also in pigs and the like, the sperm diluent of the present mode is useful for improvement of breeding techniques such as breeding for improvement of the meat quality and the like by using sperm collected only from boars having good pedigrees.

Further, since seminal plasma is not used at all, there is no need to keep many boars.

Experimental Example 1

By culturing pig sperm in a $Ca^{2+}$-containing medium, the influence of $Ca^{2+}$ on phosphorylation of tyrosine residues of the sperm proteins was studied.

As the $Ca^{2+}$-containing medium, mTBM (modified Tris-buffer medium) was used. The composition of mTBM is shown in TABLE 1.

TABLE 1

| | |
|---|---|
| 11 mM | Gulucose |
| 5 mM | Sodium pyruvate |
| 113.1 mM | NaCl |
| 3 mM | KCl |
| 7.5 mM | $CaCl_2 \cdot 2H_2O$ |
| 20 mM | Tris |
| 0.1% (w/v) | BSA (Bovine Serum Albumin) |

The pig sperm to be used were collected and frozen as described below. Boars to be used for collecting sperm were kept separately in separate pigsties, and a total of 2.5 kg of feed for boars was fed a total of 2 times in the morning and evening. The pigs were inoculated with Japanese encephalitis/porcine parvovirus infection vaccine. For this study, pigs negative for antibodies against porcine reproductive and respiratory syndrome (PRRS) and Aujeszky disease were selected. Sperm collection was carried out at intervals of 1 week. Before the sperm collection, appetite, symptoms of diseases and the like were checked to confirm that the pigs are in good conditions, and sperm was then collected such that the pigs are not agitated.

A dummy sow was placed in the pigsty of each boar and the boar was mounted on the dummy sow, followed by washing the penis and the inside of the foreskin with physiological saline to remove urine. The sperm collection was carried out by the gloved-hand technique, wherein a sterile cup was covered with gauze and semen was then placed into the cup while removing the gelatinous substance, which is a jelly-like substance emitted together with semen. The collection of semen was performed for 50 to 100 mL of only the sperm-rich fraction (about 80% of the total sperm in the semen exists in the fraction), and seminal plasma was immediately removed by centrifugation from the semen after the sperm collection.

Thereafter, sperm were diluted using a pretreatment liquid, and the temperature of the resulting dilution was adjusted for 2.5 hours to 15° C., followed by removing the supernatant by centrifugation and cooling the resultant in a solution with an osmotic pressure of 400 mOsm/kg for about 1.5 hours to a temperature of 4 to 5° C. The solution was a solution prepared by adjusting the osmotic pressure of NSF (Niwa and Sasaki freezing extender; 80% (v/v), 0.31 mol Lactose monohydrate, 20% (v/v) egg yolk, 1000 U/ml penicillin G potassium, 1 mg/ml streptomycin sulfate; osmotic pressure, 300 mOsm/kg) to 400 mOsm/kg with ultrapure water. Subsequently, a cryoprotective agent and 0.15% OEP (Orvus Es Paste surfactant) were added to the dilution as a second diluent. Further, an equal amount of the secondary diluent was added to the sperm mixture. The sperm concentration (final concentration) in this case was adjusted to $1 \times 10^9$ cells/ml. After the addition of the cryoprotective agent, the temperature of the resulting mixture was kept at 4 to 5° C. for about 30 minutes, followed by freezing the mixture. For freezing of the mixture, liquid nitrogen was used. After filling a straw with the sperm mixture, the sperm was frozen for 10 minutes in liquid nitrogen vapor at a distance of about 4 cm from the surface of liquid nitrogen, and stored thereafter in liquid nitrogen.

The obtained pig frozen sperm were thawed at 60° C. for 8 seconds, and the sperm were added to a $Ca^{2+}$-containing medium (mTBM), followed by culturing the sperm. The culture was carried out for 3 hours.

Further, as Reference Example 1, the sperm were added to a seminal plasma-containing medium and cultured in the same manner as described above. Preparation of the seminal plasma-containing medium was carried out by adding seminal plasma to the above-mentioned $Ca^{2+}$-containing medium (mTBM) to a final concentration of 10% (v/v). The seminal plasma was prepared by removing sperm from the collected semen by centrifugation and further subjecting the resultant to centrifugation to remove solids from the supernatant.

Further, as Reference Example 2, the frozen-thawed sperm were added to a $Ca^{2+}$-free medium and cultured in the same manner as described above. Preparation of the $Ca^{2+}$-free medium was carried out by removing the Ca component ($CaCl_2.2H_2O$) from the above-mentioned $Ca^{2+}$-containing medium (mTBM).

After the culture, 20 μl each of the media in which the sperm were cultured was collected and stored at −80° C. to be used for detection of phosphorylation of tyrosine residues of proteins. The detection of phosphorylation of tyrosine residues was carried out by Western blotting.

The detection of phosphorylation of tyrosine residues by Western blotting was as follows. To the sperm stored at −80° C., 17 μl of an SDS sample buffer was added, and the resulting mixture was mixed by pipetting. After centrifugation at 10,000 rpm for 2 minutes, the mixture was subjected to ultrasonication for 2 minutes, followed by heating the mixture at 100° C. for 5 minutes and subjecting the resultant to electrophoresis at 100 V for about 2 hours. Proteins were transferred onto a membrane, and the membrane was blocked with TBS supplemented with 5% BSA, followed by adding an anti-phosphorylated tyrosine antibody (primary antibody, mouse IgG) which was 2.000-fold diluted with TBS (20 mM Tris-HCl, pH 7.5; 0.15 M NaCl) supplemented with 0.5% BSA and 0.1% Tween 20, and reacting the antibody with the membrane for 12 hours at 4° C. After washing the membrane for 2 hours with TBS supplemented with 0.1% Tween 20, an anti-mouse IgG antibody (secondary antibody) which was 2,000-fold diluted with TBS supplemented with 0.5% BSA and 0.1% Tween 20 was reacted with the membrane for 1 hour. The membrane was then washed with TBS supplemented with 0.1% Tween 20 for 1 hour. A coloring substrate was added to the membrane, and the reaction was allowed to proceed for 5 minutes, followed by exposing the membrane to a film.

The results of detection of phosphorylation of tyrosine residues of the sperm proteins in the sperm cultured in the respective media are shown in FIG. 1.

In the sperm cultured in the $Ca^{2+}$-containing medium, a band indicating strong protein phosphorylation was detected near the band indicated by the arrow in FIG. 1. It is thought that, in a $Ca^{2+}$-containing medium, sperm cannot maintain their normal cell membrane because of phosphorylation.

On the other hand, in the sperm cultured in the seminal plasma-containing medium in Reference Example 1, no similar band indicating phosphorylation of tyrosine residues of the sperm proteins was detected, and it is therefore thought that addition of the seminal plasma prevented occurrence of phosphorylation of tyrosine residues of the sperm proteins. Further, in the sperm cultured in the $Ca^{2+}$-free medium in Reference Example 2, a band indicating phosphorylation of proteins was detected to some extent. This is considered to have been caused, even after removal of the Ca component ($CaCl_2.2H_2O$), by influence of a small amount of $Ca^{2+}$ existing in pure water which was used for mTBM.

From the above results, it was revealed that existence of calcium ions is involved in a functional loss of sperm, and suppression of the action of $Ca^{2+}$ on sperm in a diluted frozen sperm is indispensable for improvement of the conception rate after artificial insemination.

Experimental Example 2

Tests were carried out to confirm whether or not culturing of pig sperm in a medium to which a chelating agent was added suppresses decrease in the sperm motility, the sperm acrosomal damage rate and phosphorylation of tyrosine residues of the sperm proteins.

First, the influence of addition of EDTA was studied.

Media having concentrations of EDTA of 0 mM, 3 mM, 6.3 mM and 12 mM were prepared. The 0-mM-EDTA medium and the 3-mM-EDTA medium were prepared by removing EDTA-2Na from Modena solution and adjusting the EDTA concentration to 0 mM and 3 mM, respectively. As the 6.3-mM-EDTA medium, Modena solution was used as it is. Further, the 12-mM-EDTA medium was prepared by adding EDTA-2Na to Modena solution to attain an EDTA concentration of 12 mM.

To each medium, frozen sperm were added after thawing as in Experimental Example 1, and the sperm were cultured. The culturing time was 1 hour, 3 hours or 6 hours.

After the culture, the sperm motility was calculated using a motility analyzer (computer-assisted sperm motility analysis (CASA) system). On a plate prewarmed to 38° C., 5 µl of the medium after the culture was placed, and the ratio of moving sperm was analyzed using a computer.

Figure 2:
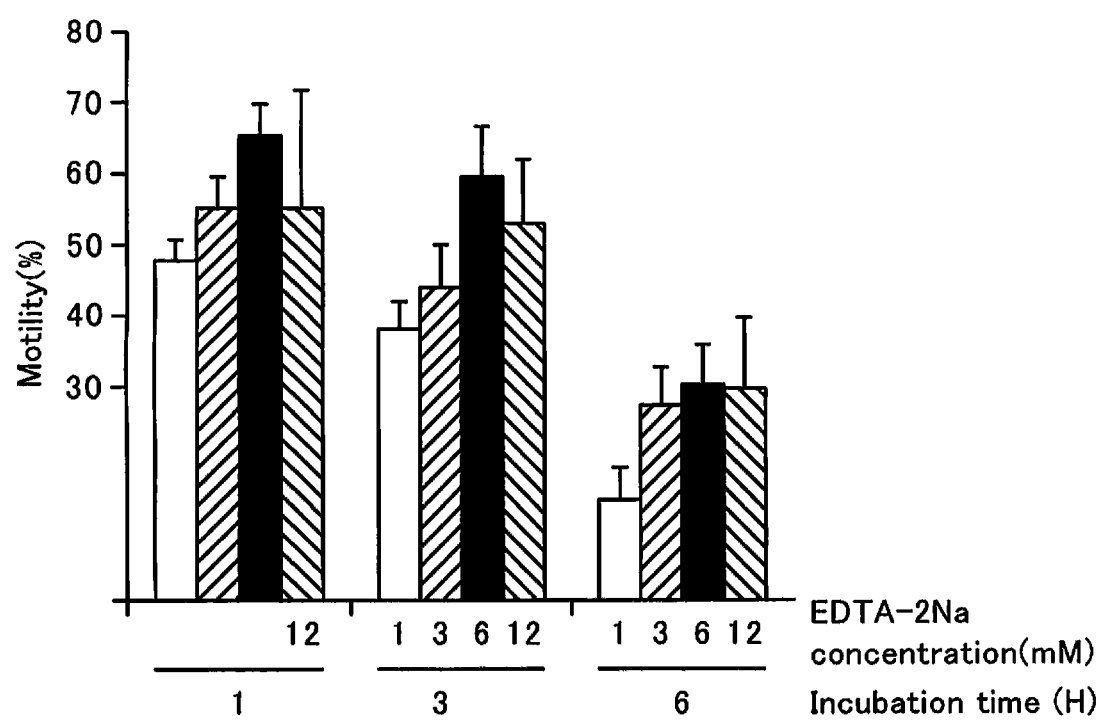
FIG. 2 is a diagram showing measurement results of the sperm motility in Experimental Example 2.

FIG. 2 shows the motility of sperm cultured under each condition.

As a result, with any culturing time, sperm cultured in the 6.3-mM-EDTA medium showed the highest sperm motility.

Subsequently, the influence of addition of EGTA was studied. In this study, sperm were cultured in a medium prepared by further adding EGTA to the 6.3-mM-EDTA medium (Modena solution), which showed the highest sperm motility as described above. After the culture, measurement of the sperm motility, detection of phosphorylation of tyrosine residues of the sperm proteins and measurement of the sperm acrosomal damage rate were carried out.

0-mM-EGTA medium, 3-mM-EGTA medium, 6-mM-EGTA medium and 9-mM-EGTA medium were prepared. As the 0-mM-EGTA medium, Modena solution was used as it is. Further, the 3-mM-EGTA medium, 6-mM-EGTA medium and 9-mM-EGTA medium were prepared by adding EGTA to Modena solution to attain EGTA concentrations of 3 mM, 6 mM and 9 mM, respectively, in the medium. Since addition of EGTA results in more acidic pH of the medium, NaOH was added to the medium to adjust pH to 7.0 to 7.1.

To each medium, frozen sperm were added after thawing as in Experimental Example 1, and the sperm was cultured. The culturing time was 1 hour, 3 hours or 6 hours.

The sperm cultured under each condition were subjected to measurement of the sperm motility, detection of phosphorylation of tyrosine residues of the sperm proteins and measurement of the sperm acrosomal damage rate.

The measurement of the sperm motility and detection of phosphorylation of tyrosine residues of the sperm proteins were carried out in the same manner as described above. The measurement of the sperm acrosomal damage rate was carried out as follows. On a slide glass, 5 µl of the medium was smeared, followed by air drying and 10 minutes of fixation with 99% methanol. After drying the methanol, marking was done with a liquid pen. FITC-peanut lectin was added to the smeared sperm (about 30 µl per sample), followed by 30 minutes of incubation at 37° C. in a moist atmosphere. Thereafter, the sperm were washed with PBS (5 minutes×3 times) and embedded in DAPI (VECTOR, VECTASHIELD with DAPI, H-1200) and then in manicure, followed by observation of the sperm.

Figure 3:
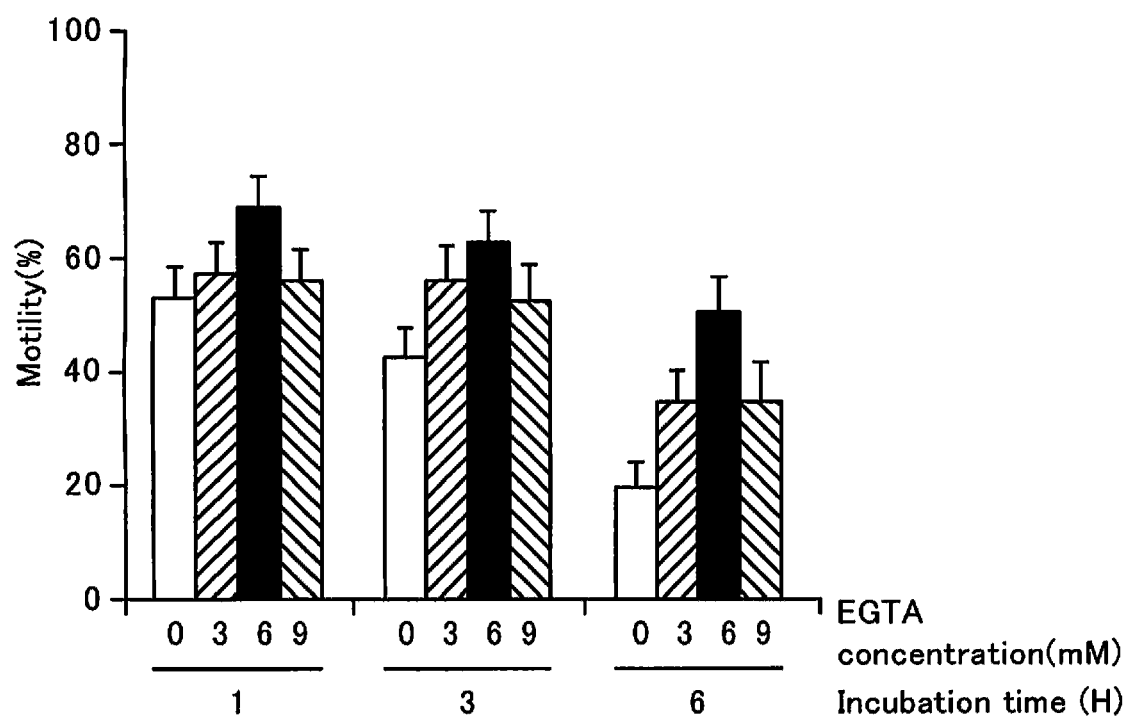
FIG. 3 is a diagram showing measurement results of the sperm motility in Experimental Example 2.
Figure 4:
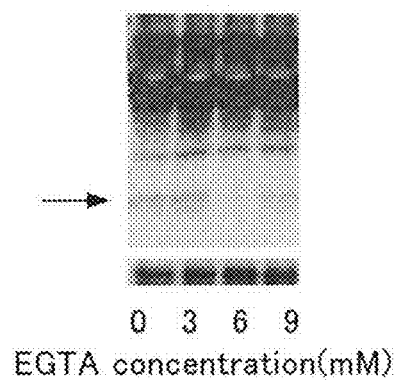
FIG. 4 is a diagram showing results of detection of phosphorylation of tyrosine residues in the sperm proteins in Experimental Example 2.
Figure 5:
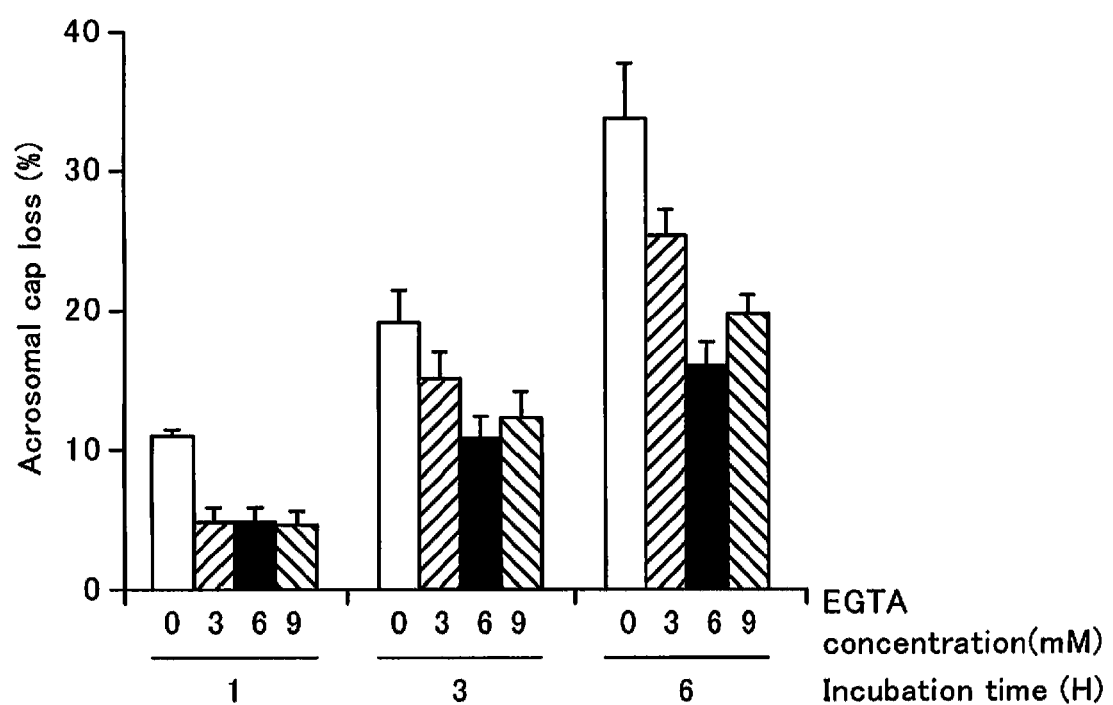
FIG. 5 is a diagram showing measurement results of the sperm acrosomal damage rate in Experimental Example 2.

The result of measurement of the sperm motility is shown in FIG. 3; the result of detection of phosphorylation of tyrosine residues of the sperm proteins after 3 hours of culture is shown in FIG. 4; and the result of measurement of the sperm acrosomal damage rate is shown in FIG. 5.

In the cases where EGTA was contained in the sperm diluent, the sperm motility was high and the sperm acrosomal damage rate was low compared to the cases where EGTA was not contained. Further, the sperm cultured in the 6-mM EGTA medium had the highest sperm motility and showed the most suppressed phosphorylation of tyrosine residues. Further, it can be seen that the sperm acrosomal damage rate was also low. From these results, it can be seen that a positive effect can be obtained in cases where the sperm diluent contains EGTA in addition to EDTA, and that the maximum effect is observed when EGTA is contained at a concentration of about 6 mM.

Further, calcium ions incorporated into the sperm cells were observed.

To each of an EDTA-containing medium and EDTA/EGTA-containing medium, pig frozen sperm after thawing were added. As the EDTA-containing medium, Modena solution was used. The EDTA/EGTA-containing medium was prepared by adding EGTA to Modena solution to adjust the EGTA concentration to 6 mM.

To each medium, 5 µM FLUO3/AM and 0.02% Pluronic F127 were added, and the sperm were cultured at 37° C. for 30 minutes in a dark room, thereby allowing FLUO3 to be incorporated into the sperm cells.

Figure 6:
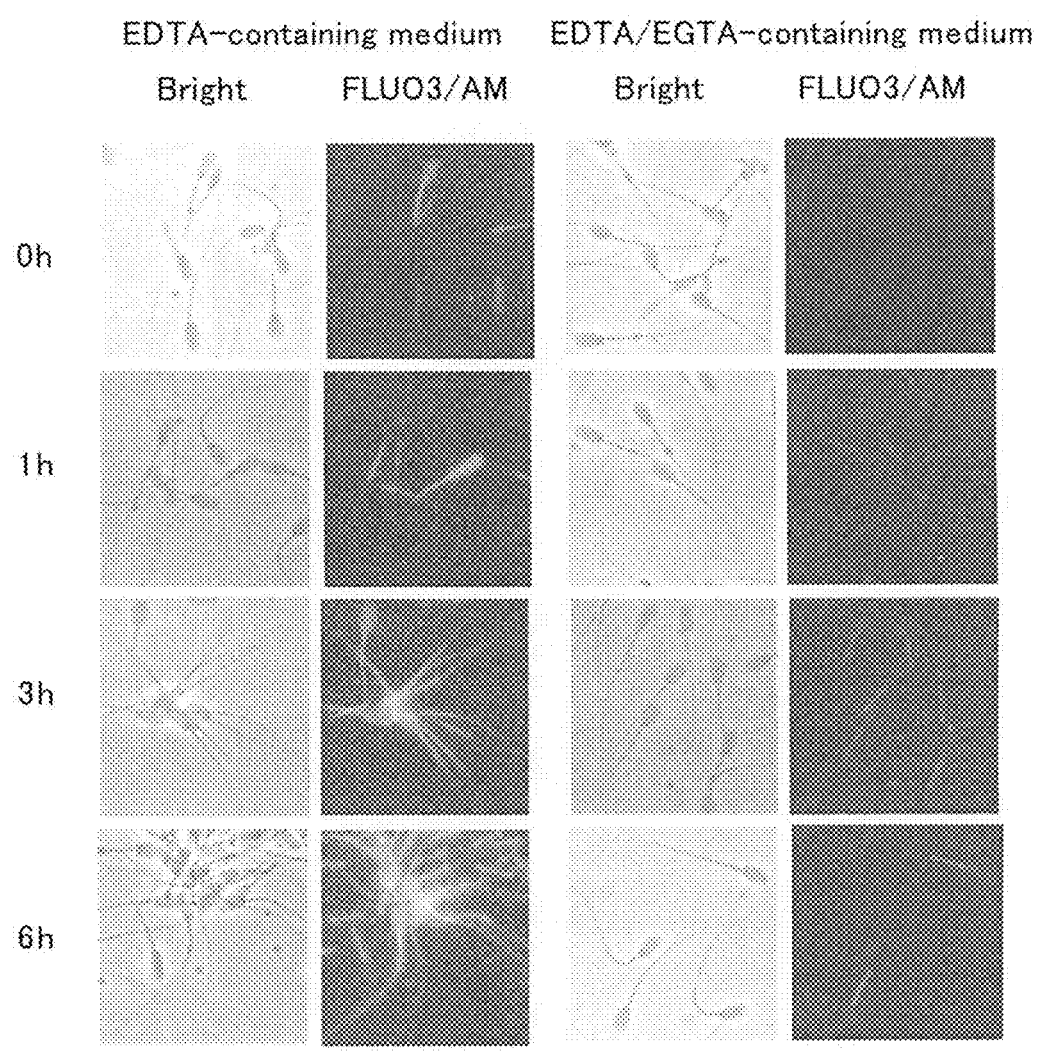
FIG. 6 is a diagram showing observation results of calcium ions incorporated into sperm in Experimental Example 2.

Thereafter, the supernatant was removed by centrifugation, and a fresh aliquot of each medium was added to the sperm. Thereafter, 5 µl of each medium was removed onto a slide, and the sperm were observed under a fluorescence microscope. The results are shown in FIG. 6.

FLUO3 is a substance which emits fluorescence by binding to a calcium ion. When calcium ions existing in the medium are incorporated into sperm cells, FLUO3 is bound to a calcium ion, resulting in emission of green fluorescence. As can be seen in FIG. 6, for each culturing time, the sperm cultured in the EDTA-containing medium showed stronger emission than the sperm cultured in the EDTA/EGTA-containing medium. The sperm cultured in the EDTA-containing medium showed very strong emission especially when the culturing time was long, but the sperm cultured in the EDTA/EGTA-containing medium only showed weak emission from the middle piece. It can be seen that incorporation of calcium ions in the medium into the sperm could be suppressed with EGTA.

Subsequently, the frozen-thawed sperm were cultured in an EDTA-containing medium, EDTA/EGTA-containing medium and seminal plasma-containing medium, and the sperm cultured in each medium were subjected to detection of phosphorylation of tyrosine residues and measurement of the sperm motility.

As the EDTA-containing medium, Modena solution (6.3 mM EDTA) was used as it is. The EDTA/EGTA-containing medium was prepared by adding EGTA to Modena solution to adjust the EGTA concentration to 6 mM. The seminal plasma-containing medium was prepared by adding seminal plasma to Modena solution to a final concentration of 10% (v/v). The frozen sperm were thawed and added to each medium, followed by culturing the sperm for 1 hour.

Figure 7:
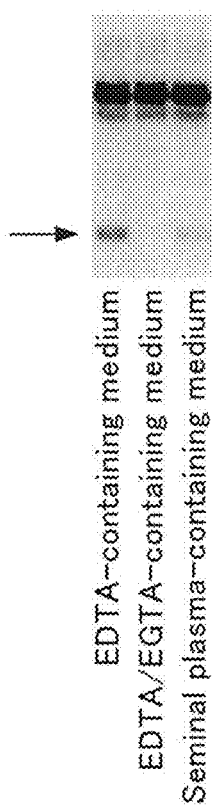
FIG. 7 is a diagram showing results of detection of phosphorylation of tyrosine residues in the sperm proteins in Experimental Example 2.

The sperm cultured in each medium were subjected to detection of phosphorylation of tyrosine residues of the sperm proteins. The results are shown in FIG. 7.

In the sperm cultured in the EDTA-containing medium and the seminal plasma-containing medium, weak bands indicating phosphorylation of proteins were detected at the position indicated by the arrow, while in the sperm cultured in the EDTA/EGTA-containing medium, no band indicating phosphorylation of proteins was detected at all at the same position, suggesting that phosphorylation of proteins was completely suppressed.

Further, the sperm after culturing in each medium were subjected to measurement of the sperm motility. The results are shown in FIG. 8.

Figure 8:
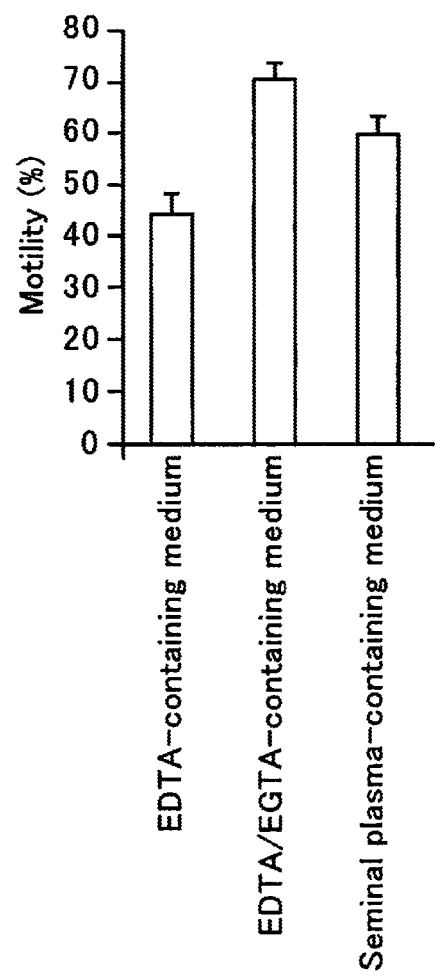
FIG. 8 is a diagram showing measurement results of the sperm motility in Experimental Example 2.

In the results showing the sperm motility in FIG. 8, a higher motility was observed for the sperm cultured in the EDTA/EGTA-containing medium compared to the sperm cultured in the seminal plasma-containing medium.

Thus, in the sperm cultured in the EDTA/EGTA-containing medium, since phosphorylation of tyrosine residues of proteins did not occur, the cell membrane of the sperm after thawing was normal, and improvement of the sperm motility was also observed. Thus, it can be seen that, by inclusion of a chelating agent which forms a complex with a calcium ion such as EDTA/EGTA in a base diluent, a seminal-plasma-free sperm diluent can be prepared.

From the above experimental results, it was demonstrated that calcium ions are involved in activation of sperm and damage of the acrosome due to phosphorylation of tyrosine residues of proteins after thawing of frozen sperm, and that addition of EDTA and/or EGTA, which chelate a calcium ion, to a diluent enables suppression of increase in calcium ions in the sperm cells and hence of activation of the sperm and damage of the acrosome, which suppression results in maintenance of the motility of the sperm.

Example 1

Using artificial semen prepared by adding pig frozen sperm to a sperm diluent containing EDTA and EGTA, artificial insemination of pigs was carried out.

EGTA was added to Modena solution to prepare a sperm diluent. The concentration of EDTA was 6.3 mM and the concentration of EGTA was 6 mM. Thereafter, as in Experimental Example 2, NaOH was added to the diluent to adjust pH to 7.0 to 7.1.

Frozen sperm were thawed at 60° C. for 8 seconds and added to the sperm diluent immediately thereafter, to prepare artificial semen (hereinafter referred to as artificial semen A1). The concentration of sperm was $1 \times 10^8$ sperm/ml.

The sows to be subjected to artificial insemination were prepared by injection of 1,000 IU/individual of serum gonadotropin (PMSG) and then administration of 750 IU/individual of human chorionic gonadotropin (hCG) 72 hours after the injection of PMSG, thereby inducing superovulation. Artificial insemination was carried out 40 hours after the administration of hCG, by injecting about 50 ml (total sperm number, 5 billion) of artificial semen A1 prepared as described above to the uterus of a sow.

On Day 21 after the artificial insemination, fetuses were confirmed on a monitor in ultrasonic pregnancy diagnosis. The reason why the confirmation was carried out on Day 21 was that, since estrus occurs in a pig at intervals of 21 days, existence of unfertilized eggs or degenerated fertilized eggs results in appearance of a sign of estrus in the genital region upon diagnosis of pregnancy on Day 21 after fertilization.

Further, whether the return has occurred was confirmed by the non-return method at the same time on Day 21, thereby diagnosing pregnancy.

Further, as a Reference Example, artificial insemination was carried out in the same manner as described above using an artificial semen (hereinafter referred to as artificial semen B1) prepared by thawing frozen sperm in the same manner as described above in a seminal-plasma-containing diluent prepared by adding seminal plasma to Modena solution (10% (v/v) seminal plasma).

Subsequently, the conception rate and the implantation rate were measured for each artificial semen. The conception rates are shown in TABLE 2, and the implantation rates are shown in TABLE 3. The conception rate was calculated by counting the number of individuals with which artificial insemination was carried out and the number of individuals which became pregnant. Further, the implantation rate was calculated by counting the total number of corpus luteum and the total number of fetuses in the uterus in 6 individuals of sows.

TABLE 2

|  | Number of individuals with which insemination was carried out | Number of individuals which became pregnant | Conception rate (%) |
|---|---|---|---|
| Artificial semen A1 | 10 | 9 | 90 |
| Artificial semen B1 | 12 | 10 | 83 |

TABLE 3

|  | Total number of corpus luteum | Total number of fetuses in the uterus | Implantation rate (%) |
|---|---|---|---|
| Artificial semen A1 | 130 | 66 | 51 |
| Artificial semen B1 | 100 | 78 | 78 |

In the case of the artificial semen A1 containing EDTA/EGTA, the conception rate was 90%, which was a high value equivalent to the conception rate in the case of the artificial semen B1 containing 10% seminal plasma.

However, the implantation rate was 51%, which was lower than the implantation rate of 78% in the case of the artificial semen B1 containing 10% seminal plasma, and most fetuses had been phagocytosed. Further, in the case of artificial insemination using the artificial semen A1, oviduct flushing of 3 individuals of sows resulted in a total number of corpus luteum of 51 and a number of fetuses in the uterus of 42, indicating a fertility in the oviduct of 82%. Therefore, without phagocytosis of the fetuses, the implantation rate may have been similar to the implantation rate observed with the artificial semen B1. It is thought that, in the case of artificial insemination using the artificial semen A1, fetuses were phagocytosed due to failure of the intrauterine immunity after fertilization.

Experimental Example 3

From the results in Example 1, it is thought that existence of seminal plasma is required for sperm to achieve the intrinsic fertilization function and for further improvement of the implantation rate, and that seminal plasma contains immunosuppressive factors by which phagocytosis of sperm can be suppressed. Thus, attempts were made to identify immunosuppressive factors in seminal plasma.

Seminal plasma was collected from 17 individuals of boars, and steroid hormones in the seminal plasma were measured using the EIA method. Further, using a membrane antibody array (PROTEOME PROFILER™ Array, Human Cytokine Array Panel A, ARY005, available through R&D Systems, Inc., Minneapolis, MN), cytokines in the seminal plasma were detected.

Figure 9:
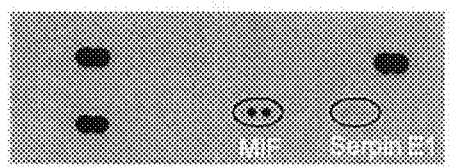
FIG. 9 is a diagram showing results of detection of cytokines in seminal plasma in Experimental Example 3.

The result of measurement of steroid hormones in the seminal plasma is shown in TABLE 4, and the result of detection of cytokines in the seminal plasma is shown in FIG. 9.

TABLE 4

| | Cortisol (ng/ml) |
|---|---|
| In seminal plasma | 0.92 |

As shown in TABLE 4, 0.92 ng/ml cortisol was detected in the seminal plasma. Further, as indicated by the circles in FIG. 9, MIF and Serpin E1 were detected. On the membrane shown in FIG. 9, 3 locations (upper left, lower left and upper right) always emit light, and a total of 36 types of specific anti-cytokine antibodies are arranged at other locations, in each of which one of the antibodies is plotted at 2 positions. In cases where a cytokine specifically reactive with a plotted anti-cytokine antibody exists, the location where the antibody was plotted emits light.

From the above results, it was identified that the seminal plasma contains the immunosuppressive factors cortisol, MIF and Serpin E1. It is thought that inclusion of these factors in a diluent can realize improvement of the implantation rate.

EXAMPLE 2

An artificial semen was prepared by adding pig frozen sperm to a sperm diluent containing cortisol, EDTA and EGTA and used to perform artificial insemination of pigs.

First, cortisol and EGTA were added to Modena solution to prepare a sperm diluent. The concentration of cortisol was 100 ng/mL; the concentration of EDTA was 6.3 mM; and the concentration of EGTA was 6 mM. As in Example 1, NaOH was added to the diluent to adjust pH to 7.0 to 7.1.

Frozen sperm were thawed at 60° C. for 8 seconds and added to the sperm diluent immediately thereafter, to prepare artificial semen (hereinafter referred to as artificial semen A2). The concentration of sperm was $1 \times 10^8$ sperm/mL.

Using the prepared sperm diluent, artificial insemination was carried out. The method was the same as in Example 1 except that PMSG was not administered to the sow.

Further, in the same manner as in Example 1, artificial insemination was carried out using the artificial semen A1 prepared by diluting frozen sperm with a sperm diluent to which EDTA and EGTA were added.

The conception rate and the implantation rate are shown in TABLE 5. The conception rate was calculated by counting the number of individuals of sows with which artificial insemination was carried out and the number of individuals of sows which became pregnant. Further, the implantation rate was calculated by counting the total number of fetuses in the uterus and the total number of corpus luteum in 4 individuals of sows, followed by dividing the values by the number of individuals.

TABLE 5

| | Conception rate (%) | Number of fetuses in the uterus (/individual) | Implantation rate (%) |
|---|---|---|---|
| Artificial semen A1 | 90 | 11.0 | 51 |
| Artificial semen A2 | 92 | 12.5 | 83* |

The conception rate in the case of artificial insemination using the sperm diluent containing cortisol was 92%, which was higher than the rate obtained with the cortisol-free sperm diluent, and further, the implantation rate was 83%, which was much higher than the rate of 51% obtained with the cortisol-free sperm diluent.

Figure 10:
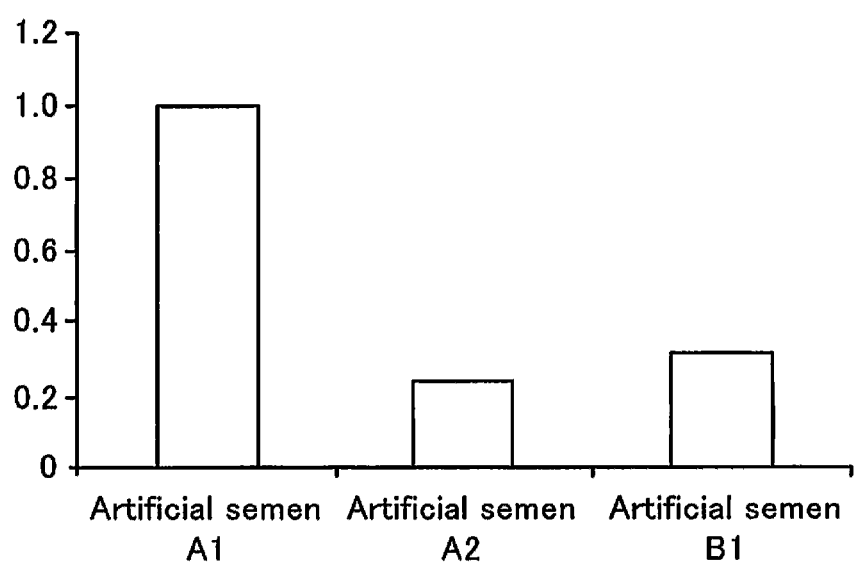
FIG. 10 is a diagram showing relative values of the leukocyte count in the uterus in Example 2.

Further, measurement of the leukocyte count in the uterus after the artificial insemination revealed that, as indicated by the relative values of the leukocyte count in the uterus in FIG. 10, the leukocyte count in the uterus in the case of the artificial semen A2 was much smaller than in the case of the artificial semen A1, and further, even smaller than in the case of the artificial semen B1 in Example 1, in which seminal plasma was used. Thus, it can be seen that the immunosuppressive action of cortisol suppressed phagocytosis of embryos after the fertilization, resulting in the enhanced implantation rate.

Although the above adrenocortical hormone (a steroid hormone such as cortisol) is usually injected at a dose of 5 to 50 mg per individual for therapy of livestock, only 5 μg was injected to the uterus in the artificial insemination of the present Example. Thus, since this dose is about 1,000 to 10,000 times smaller than the dose in the cases of therapeutic use, it is thought that the meat of the mother pig and the fetuses in the uterus are not affected. Actually, in terms of the mother pigs to which artificial insemination was carried out using the sperm diluent, 4 individuals are in the second month of pregnancy and 6 individuals are in the first month of pregnancy at present, without experiencing any abnormal health condition of the mother pigs or abortion. Further, even after the delivery, no deformed piglet was found, and therefore there was no harmful influence of the addition of cortisol.

As indicated by the above experimental results, preparation of a seminal plasma-free sperm diluent was realized.

The present application is based on Japanese Patent Application No. 2009-144703, filed on Jun. 17, 2009. The entire description, claims and figures in Japanese Patent Application No. 2009-144703 are incorporated in the present description as references.

INDUSTRIAL APPLICABILITY

As described above, the sperm diluent contains a chelating agent which forms a complex with a calcium ion. Further, the sperm diluent contains an immunosuppressive factor which suppresses migration of leukocytes. By adding frozen sperm to this sperm diluent followed by performing artificial insemination, the sperm can reach eggs without dying, and the sperm and embryos are not phagocytosed by leukocytes, resulting in a high conception rate and a high implantation rate. The sperm diluent can be suitably employed in industries such as the livestock industry wherein non-human mammals are bred, and especially effectively employed for breeding of multiparous animals such as pigs by artificial insemination.

The invention claimed is:

1. A pig sperm diluent comprising chelating agents which form a complex with a calcium ion, and an immunosuppressive factor which suppresses migration of leukocytes; the chelating agents being 3 to 9 mM of ethylene glycol tetraacetic acid and 3 to 9 mM of ethylenediaminetetraacetic acid, the immunosuppressive factor being cortisol.

2. The pig sperm diluent according to claim 1, which is used for diluting frozen sperm prepared by removal of seminal plasma and freezing.

3. A method for artificial insemination of a pig, comprising:
    preparing frozen sperm by removing seminal plasma from semen collected from a pig and, upon melting, diluting the sperm with the pig sperm diluent according to claim 1, to prepare artificial semen; and injecting said artificial semen into a uterus of a female pig to carry out artificial insemination.

4. The pig sperm diluent according to claim 1, wherein the cortisol is in an amount of 100 ng to 10,000 ng.

* * * * *